(12) United States Patent
Dvorak et al.

(10) Patent No.: US 7,337,123 B2
(45) Date of Patent: Feb. 26, 2008

(54) RULES BASED TICKETING FOR SELF-SCHEDULING OF APPOINTMENTS

(75) Inventors: Carl D. Dvorak, Madison, WI (US); Sumit S. Rana, Madison, WI (US)

(73) Assignee: Epic Systems Corporation, Verona, WI (US)

( * ) Notice: Subject to any disclaimer, the term of this patent is extended or adjusted under 35 U.S.C. 154(b) by 966 days.

(21) Appl. No.: 09/829,292

(22) Filed: Apr. 9, 2001

(65) Prior Publication Data

US 2003/0208391 A1 Nov. 6, 2003

Related U.S. Application Data

(60) Provisional application No. 60/263,651, filed on Jan. 23, 2001, provisional application No. 60/214,290, filed on Jun. 26, 2000.

(51) Int. Cl.
*G06F 15/02* (2006.01)

(52) U.S. Cl. .................... 705/8; 705/3; 705/9; 709/204

(58) Field of Classification Search .................... 705/8
See application file for complete search history.

(56) References Cited

U.S. PATENT DOCUMENTS

| | | |
|---|---|---|
| 5,471,382 A | 11/1995 | Tallman et al. |
| 5,666,492 A | 9/1997 | Rhodes et al. |
| 5,692,125 A | 11/1997 | Schloss et al. |
| 5,740,800 A | 4/1998 | Hendrickson et al. |
| 5,748,907 A * | 5/1998 | Crane .......................... 705/2 |
| 5,758,095 A | 5/1998 | Albaum et al. |
| 5,833,599 A | 11/1998 | Schrier et al. |
| 5,842,976 A | 12/1998 | Williamson |
| 5,845,253 A | 12/1998 | Rensimer et al. |

(Continued)

FOREIGN PATENT DOCUMENTS

WO    WO-98/13783    4/1998

(Continued)

OTHER PUBLICATIONS

Ho, Chrwan-jyh; Lau, Hon-Shiang; Li, Jing. Introducing variable-interval appointment scheduling rules in service systems. International Journal of Operations and Production Mangement v15n6. 1995. from dialog.*

(Continued)

*Primary Examiner*—Romain Jeanty
*Assistant Examiner*—Dave Robertson
(74) *Attorney, Agent, or Firm*—Boyle Fredrickson S.C.

(57) ABSTRACT

A system to allow self-scheduling of appointments via an electronic network. The electronic network is configured to permit secure access thereto by a service recipient. The system comprises a self-scheduling server coupled to the electronic network for secure communications therewith. The self-scheduling server is adapted to receive appointment scheduling requests from the service recipient securely via the electronic network The self-scheduling server includes a processor which is coupled to a rule base, to a scheduling database, and receives the appointment scheduling requests. The processor is operable upon the appointment scheduling requests to authorize the appointment scheduling request to send appointment schedule information to the scheduling database for inclusion therein and to send an appointment acknowledgment to the service recipient securely via the electronic network.

12 Claims, 3 Drawing Sheets

U.S. PATENT DOCUMENTS

| | | | |
|---|---|---|---|
| 5,929,851 A | 7/1999 | Donnelly | |
| 5,960,406 A | 9/1999 | Rasansky et al. | |
| 5,974,389 A | 10/1999 | Clark et al. | |
| 5,997,476 A | 12/1999 | Brown | |
| 6,029,138 A | 2/2000 | Khorasani et al. | |
| 6,081,786 A | 6/2000 | Barry et al. | |
| 6,154,726 A | 11/2000 | Rensimer et al. | |
| 6,249,809 B1* | 6/2001 | Bro | 709/217 |
| 6,275,150 B1 | 8/2001 | Mandler et al. | |
| 6,283,761 B1* | 9/2001 | Joao | 434/236 |
| 6,317,719 B1 | 11/2001 | Schrier et al. | |
| 6,345,260 B1* | 2/2002 | Cummings et al. | 705/8 |
| 6,389,454 B1* | 5/2002 | Ralston et al. | 709/204 |
| 6,678,613 B2* | 1/2004 | Andrews et al. | 701/213 |
| 6,757,898 B1* | 6/2004 | Ilsen et al. | 709/203 |
| 7,028,178 B2* | 4/2006 | Orlick | 713/150 |
| 7,056,289 B2* | 6/2006 | Kasper et al. | 600/300 |
| 7,188,073 B1* | 3/2007 | Tam et al. | 705/9 |
| 2001/0011225 A1* | 8/2001 | O'Connor et al. | 705/9 |
| 2001/0021910 A1* | 9/2001 | Goldstein | 705/2 |
| 2001/0039504 A1* | 11/2001 | Linberg et al. | 705/3 |
| 2001/0049610 A1 | 12/2001 | Hazumi | 705/3 |
| 2002/0059082 A1* | 5/2002 | Moczygemba | 705/3 |
| 2002/0062229 A1 | 5/2002 | Alban et al. | |
| 2002/0116220 A1* | 8/2002 | Glazier | 705/2 |
| 2002/0188478 A1 | 12/2002 | Breeland et al. | |
| 2003/0061072 A1 | 3/2003 | Baker et al. | |
| 2003/0110059 A1 | 6/2003 | Janas, III et al. | |
| 2003/0195774 A1* | 10/2003 | Abbo | 705/3 |
| 2005/0055252 A1* | 3/2005 | Todd | 705/5 |

FOREIGN PATENT DOCUMENTS

| | | |
|---|---|---|
| WO | WO-99/41682 A2 | 8/1999 |
| WO | WO-00/28460 | 5/2000 |
| WO | WO-00/29983 | 5/2000 |
| WO | WO 00/73952 A1 * | 12/2000 |
| WO | WO 0167731 A2 * | 9/2001 |
| WO | WO-02/29664 A1 | 4/2002 |

OTHER PUBLICATIONS

Beckham, J. Daniel. The engine of choice. Healthcare Forum Journal v39n4. Jul./Aug. 1996. from dialog.*

Merriam-Webster's Medical Office Handbook, 2nd Edition, 1996, pp. 206-211.*

Aymond, Ron. "22 Tips for Improving Your Practice", Family Practice Management, Sep. 1999, vol. 6, No. 8, pp. 20-24.*

Brown, Sanford J. "The Disgruntled Patient", Family Practice Management, Jun. 1999, vol. 6, No. 6, p. 44.*

Daley et al ("Improving compliance with the initial outpatient session among discharged inpatient dual diagnosis clients," Social Work, 1998, v43, n5, pp. 470-474.*

Mercando, A. D., Appointment Scheduling on Computer, PACE, Jul. 1997, pp. 1860-1862, vol. 20.

"HCS Order Communications Module," web.archive.org/hcsinteractant.com, 2000, pp. 1-3.

Ebida et al., "Getting Data Out of the Electronic Patient Record: Critical Steps in Building a Data Warehouse for Decision Support," SIMS University Health Network, Dept. of Medicine, University of Toronto, Canada, Nov. 8, 1999, pp. 1-5.

"Patient1 Vista", PerSe Technologies, www.per-se.com/web.archive.org, 2000, 2 pages.

"Sunrise Clinical Manager", Eclipsys, Sunrise Clinical Overview, www.eclipsnet.com/web.archive.org, 1999, 1 page.

"American Medical Management Selects Tandem Computers as Systems Partner", PR Newswire, Feb. 20, 1997, 2 pages.

"Premier Members Select Cerner's Clinical Data Repository as a Result of Exclusive Endorsement", PR Newswire, Feb. 19, 1997, 2 pages.

"Physicians and Staff Go Online with Cerner's Clinical Data Repository and Orders Management", PR Newswire, Mar. 4, 1996, 2 pages.

"Patient1", PerSe Technologies, www.per-se.com/web.archive.org, 2000, 4 pages.

Egan et al., "Computers and Networks in Medical and Healthcare Systems," Comput. Biol. Med., vol. 25, No. 3, 1995, pp. 355-365.

Plaisant et al., "An Information Architecture to Support the Visualization of Personal Histories," Information Processing & Management, vol. 34, No. 5, 1998, pp. 581-597.

Van De Velde, "Framework for a Clinical Information System," International Journal of Medical Informatics, vol. 57, 2000, pp. 57-72.

Fabbretti et al., "Applying the Object Paradigm to a Centralized Database for a Cardiology Division," International Journal of Bio-Medical Computing, vol. 42, 1996, pp. 129-134.

Michihiro Hazumi and Toshio Kawamoto, "Development of Electronic Medical Record System," *NEC Res. & Develop.*, vol. 41, pp. 102-105, Jan. 2000.

* cited by examiner

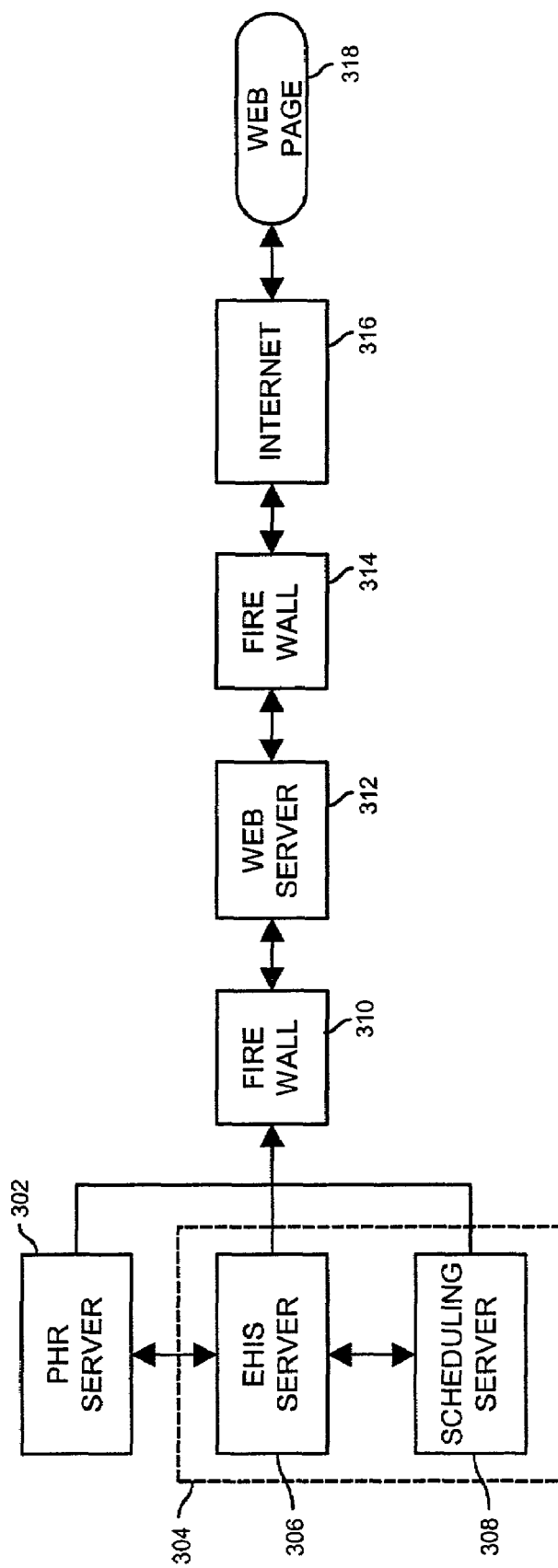

RULES BASED TICKETING FOR SELF-SCHEDULING OF APPOINTMENTS

CROSS-REFERENCE TO RELATED APPLICATIONS

This application claims priority to U.S. Provisional Application Ser. No. 60/263,651, entitled "Rules Based Ticketing For Self-Scheduling Of Appointments," filed Jan. 23, 2001 and U.S. Provisional Application Ser. No. 60/214,290, entitled "Integrated Patient and Enterprise Health Record System," filed Jun. 26, 2000, the disclosures of which are hereby expressly incorporated herein by reference.

FIELD OF THE INVENTION

The present invention relates generally to health record management, and more particularly, the present invention relates to a rules-based scheduling system to allow a healthcare facility to control appointments scheduled through the Internet with "scheduling tickets" that incorporate a variety of rules.

BACKGROUND OF THE INVENTION

Many attempts have previously been made to streamline the process of scheduling appointments for patients in the healthcare industry. From a healthcare organization's point of view the most efficient method is to let patients schedule appointments themselves. However, until the advent of the Internet, this solution was not feasible. Now, the Internet has provided patients with direct access to an organization through the web, thereby opening up the possibility of self-scheduling. Nevertheless, self-scheduling over the Internet presents unique and interesting problems. For example, there are always security issues when dealing with medical information on the Internet. Also, if the system is not implemented properly, patients could abuse the system. Furthermore, Healthcare providers, such as doctors, nurses, and surgeons often have concerns that they are losing control of their daily schedules if they allow patients to schedule their own appointments.

The existing scheduling solutions are based on messaging or very restricted access. These solutions allow patients to enter some limited information concerning an appointment. Some examples are: (1) which provider the patient wants to see, (2) the day and time the patient wants to be seen, (3) some of the patient's insurance information, and (4) a few other types of information relevant to scheduling.

After requests were submitted in the previous systems, workers at the clinics were then required to review each of the requests and contact every patient individually to inform him or her whether or not the request was granted. While this process is somewhat convenient for the patients, it does not automatically schedule appointments or immediately enter the data into the organization's system. Rather, it relies on human intervention to evaluate the requests and contact the patients when the decision to schedule the appointment has been made.

There is a demonstrated need for healthcare organizations to allow the full scheduling of appointments over the Internet in an automated process that gives patients immediate results and eliminates the need for employees of the facility to review each request for an appointment. None of the previous systems satisfied this need.

BRIEF DESCRIPTION OF THE DRAWINGS

FIG. 3 is a flowchart illustrating the components and connections from the enterprise healthcare information management system through the Internet and on to the patient via a web page portal.

DETAILED DESCRIPTION OF THE PREFERRED EMBODIMENTS

Figure 1:
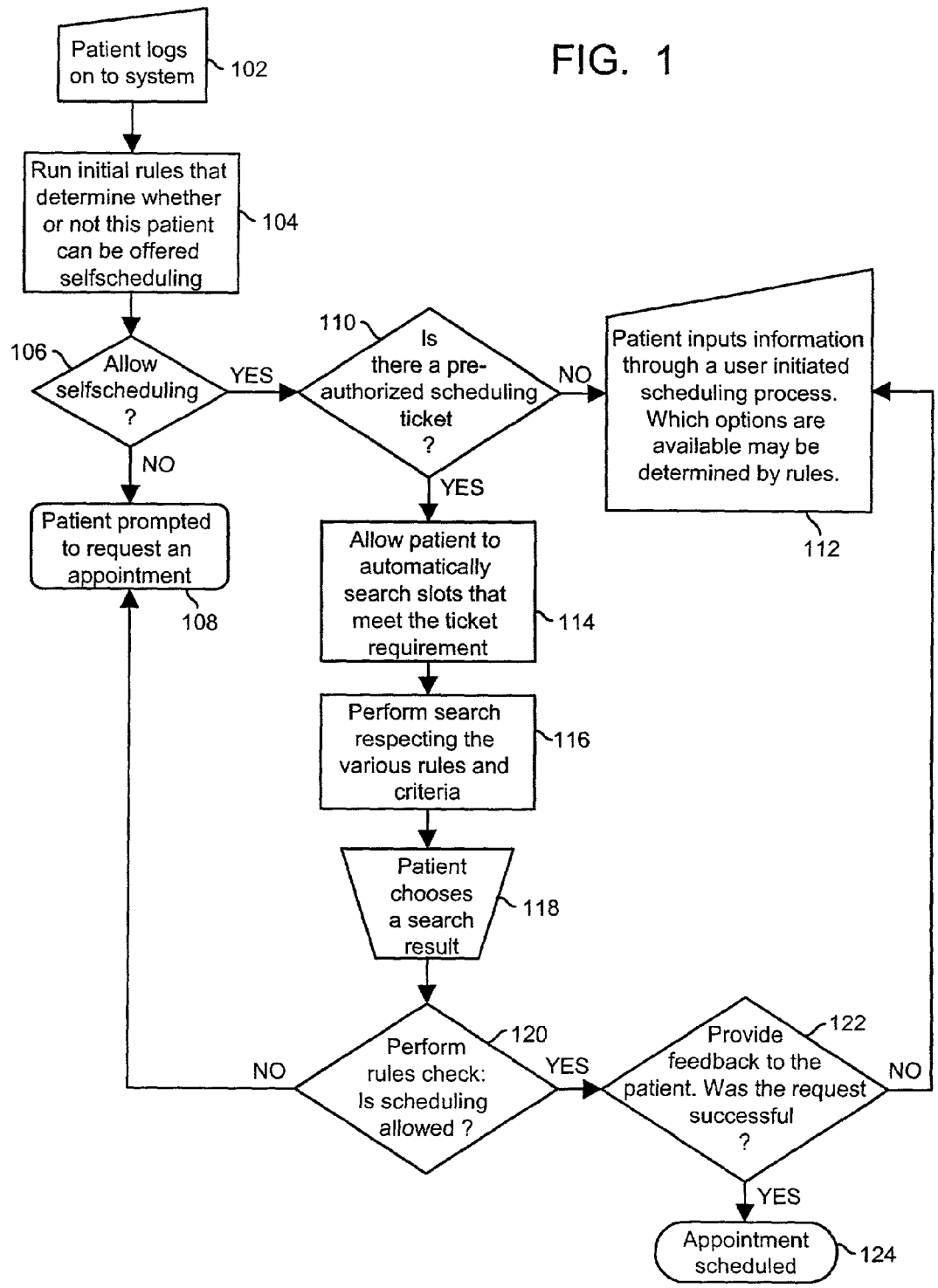
FIG. 1 is a flow chart representation of the path that the system would take when a patient attempted to schedule an appointment directly from the system.

According to a preferred embodiment of the invention a system that enables a patient to use a pre-authorized or a user initiated scheduling process that utilizes hierarchically-layered rules. The system further provides dynamic feedback to self-schedule appointments with a user's preferred clinics and providers in a confidential and secure manner.

The rules based ticketing system for self-scheduling provides healthcare clinics and providers the ability to manage and control patient appointment utilization. For several reasons, it is very desirable from a healthcare provider's perspective to allow patients to schedule their own appointments. It is also desirable from a patient's perspective to be able to independently schedule their own appointments at their convenience through the Internet. A system according to the preferred embodiments of the invention satisfies the desires of both parties.

A rules-based scheduling system according to a preferred embodiment of the invention allows a facility to control appointments scheduled through the Internet with "scheduling tickets" that incorporate a variety of rules and triggers. These rules can be defined as many things. Some examples that may be included are:

(1) The type of patient. The system checks if the patient has any special conditions, such as being diabetic or undergoing cancer therapy, that would allow or disallow a patient to self-schedule. A clinic may not want certain patient types scheduling their own appointments because some patients need special consideration.

(2) A patient's Insurance. The system checks to ensure that patients have insurance or other methods to cover their medical expenses.

(3) Referral information. The system checks to ensure that patients do not have any outstanding referrals for that type of visit so that appointments are not duplicated.

(4) Previous visits of a certain type. The system checks if patients are due for or require a follow up appointment. For example, a minor operation may warrant a return visit to remove the sutures.

(5) Provider preferences. The system takes into account when providers can or want to see certain types of patients. For example, if a provider does not want to schedule physicals in the morning, the system could reject any ticket submission from patients to have physicals scheduled in the morning for this particular provider.

(6) Patient preferences. The system takes into account when patients want to be seen by their providers.

(7) Past patient history. The system checks if factors exist that may change whether or not a patient can self-schedule. For instance, a system could deny a patient the right to self-schedule because he has a history of more than 20% no-shows or cancellations.

(8) Copay requirements. The system checks if a copay by the patient is required for the appointment. Accordingly, the system requires that a patient must pay the copay when he or she schedules the appointment.

These rules could further be set up as a layered hierarchy. They could be specified at various levels which include, but are not limited to:

(1) System level or facility level. This is the least specific level. The settings at this level pertain to an entire healthcare facility.

(2) Department level. This level is more specific than the system level. The settings at this level pertain to all providers who work in a specific department of a facility.

(3) Provider level. This level is very specific. The settings at this level pertain to only a specific provider.

(4) Rule level. The specificity of this level could vary, depending on how a facility has set up the system. For example, one facility could set up the rules level settings as overriding settings at the provider level, while another facility could set up settings at the provider level as overriding the settings at the rules level. The settings at this level pertain to only a specific rule.

Rules set at more specific levels could override rules set at less-specific levels. For example, if an entire clinic's system is configured to allow diabetic patients to self-schedule using pre-authorized scheduling tickets, but a diabetic patient attempts to use a scheduling ticket to schedule an appointment in a department that does not allow diabetic patients to self-schedule, the patient would not be able to self-schedule in that department because the department level is more specific than the system level, so it takes precedence. However, diabetic patients in departments that allow diabetic patients to use self-scheduling or in departments with no specific rules for diabetic patients could still schedule an appointment with a ticket.

Different rules could also be set up to override other rules. For example, provider preference rules could be set up to override patient preference rules when a patient is using a scheduling ticket to make an appointment. Also, the past patient history rules could be defined to override all other rules, because if a patient abuses self-scheduling, a facility would most likely not want that patient to be scheduling appointments, regardless of what the other rules dictate.

Furthermore, these rules can be dynamic in their ability to change over time. For example, the system could revoke a patient's ability to self-schedule if the patient abuses the system. Therefore, if a patient self-scheduled three appointments and did not show up for them, the system could automatically change the patient's status from 'able to self schedule' to 'unable to self schedule.'

While the invention is further described in terms of several preferred embodiments, it will be appreciated that the invention is not limited in scope to the embodiments herein described. Many modifications, alterations and additions may be made without departing from the fair scope of the invention.

Referring to FIG. 1 of the drawings, a flow chart representation is shown of the path that the system would take when a patient attempted to schedule an appointment directly from the system. Through the system, a patient with access to self-scheduling can, either with a pre-authorized scheduling ticket or through a user initiated scheduling process, request an appointment with his or her clinic or provider. The self schedule request would then have to pass a series of checks, or rules, before it could be fulfilled. First, the system would run 104 a rules check to see 106 if the patient is authorized to self-schedule appointments. If the patient has the appropriate authorization, the system would then check 110 to see if a preauthorized scheduling ticket existed for the patient. If one existed, the system would offer 114 the patient time slots that met the ticket requirements.

If there were no pre-authorized ticket for the patient, he or she would enter an appointment search criteria manually 112. Then the system would verify that the patient was allowed to see the search results, whether the search results were obtained using the pre-authorized ticket or using search criteria initiated by the patient. The patient would then select 118 an appointment to schedule. The system would perform 120 one last check to make sure the patient was allowed to schedule the appointment and that the appointment was still available, and then the appointment would be made 124. If the specific appointment that the patient was trying to book was unavailable, the patient would be prompted 112 to enter scheduling information manually, and the process would start over.

Again, if the scheduling ticket or the responses from the user initiated scheduling process pass all of the appropriate security checks, the system then can present the patient with a list of solutions that match his or her request. After the patient selects an appointment 118, the system can perform 120 a final check to ensure that the patient is authorized to use the ticket to schedule the appointment and that the time slot is still available. If the request passes this security check, then the system can notify 124 the patient that he or she has successfully scheduled the appointment with his or her clinic or provider. If for any reason, a patient is not allowed to self-schedule, the system could be configured 108 to immediately give the patient the option to request an appointment, as opposed to actually scheduling one with a scheduling ticket.

Figure 2:
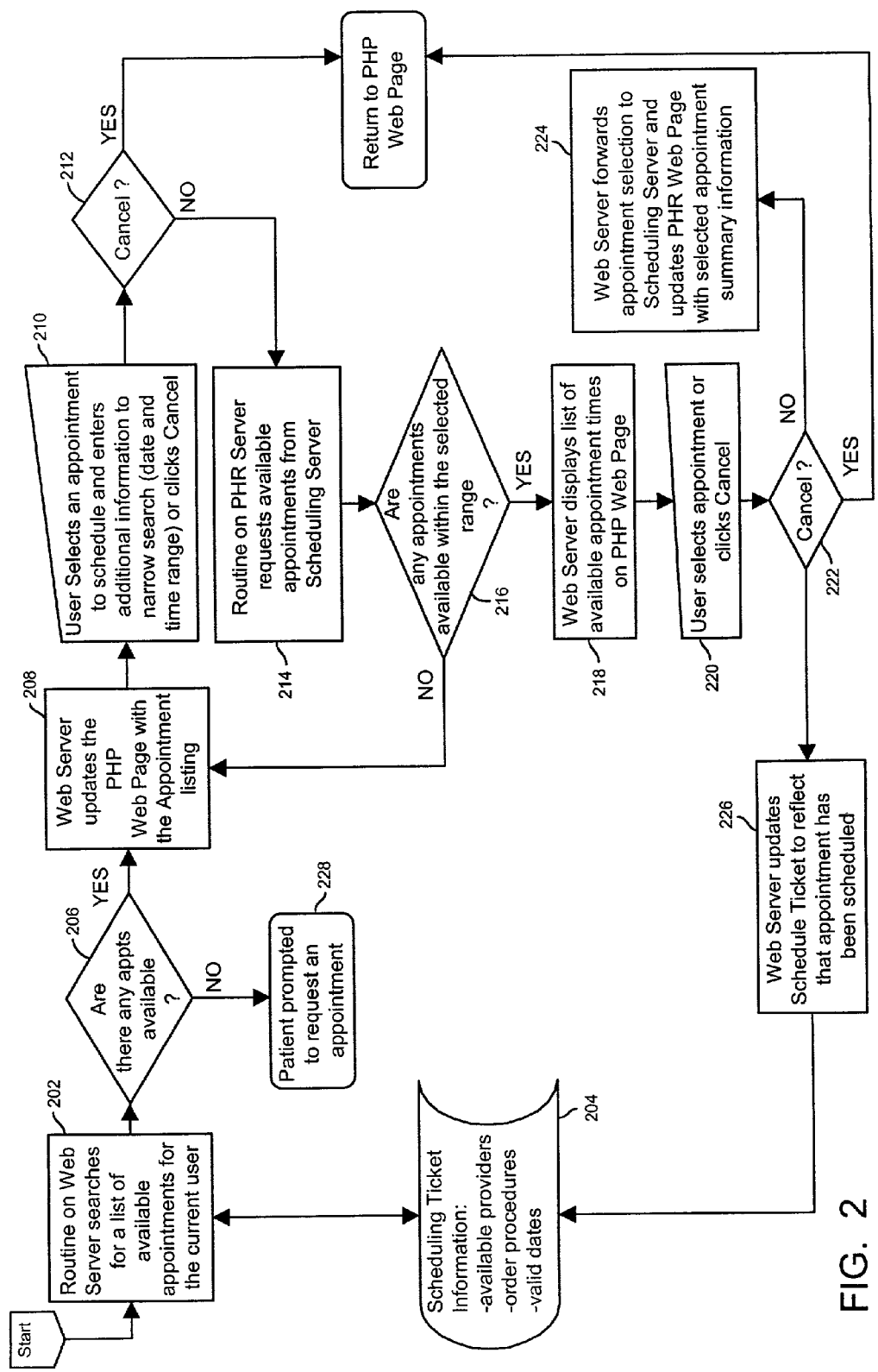
FIG. 2 is a flowchart that illustrates the process by which a user logged in to his Patient Health Portal (PHP) Web Page can schedule an appointment that has been pre-qualified.

As explained above, a patient can self-schedule an appointment with his or her clinic or provider using either a pre-authorized scheduling ticket 114 or through a user initiated scheduling process 112. As shown in FIG. 2, a pre-authorized scheduling ticket is an electronic ticket that is given to the patient via their electronic health record managed by their physician. This record is stored on a computer server and is referenced by the Internet based scheduling system to limit the patient's ability to schedule appointments to what is described 204 by the ticket.

An electronic database of scheduling tickets (also referred to as access tickets) would be created. Attributes 204 of records in this database would include the healthcare provider who authorized the ticket, the services the ticket entitles the patient to schedule (e.g. one follow up visit within the next two months), and the patient identifier for the patient the ticket is for. The ticket also has an attribute that describes its current status (unused, appointment made, appointment completed).

These pre-authorized scheduling tickets would be automatically created during the physician's documentation of a clinical encounter with the patient. Typically a doctor will document when a patient should return, in follow up of a problem (e.g. to check on how well a medication is working to control the patient's blood pressure) or for a follow up procedure (e.g. suture removal). When initially created, the ticket's status is set to "unused."

Referring again to FIG. 2, the flowchart illustrates the process by which a user logged in to his Patient Health Portal (PHP) Web Page can schedule an appointment that has been pre-qualified. The structure and functionality of a PHP Web Page is described in the commonly assigned U.S. Pat. application PCT/US01/20357 entitled "Integrated Patient and Enterprise Health Record System," the disclosure of which is hereby expressly incorporated herein by reference. When the user clicks the Schedule Appointment option, the Web Server queries 202 the Scheduling Server to see if there are any pre-qualified appointments available for the current user. If there are, the Web Server updates 208 the PHP Web Page with the available appointment information. The user can then select 210 an appointment to schedule, and indicates date, time, and locations (selections may be limited by information in the Scheduling Ticket database). The Web Server then obtains 214 appointment times available within the selected range and displays 218 them, whereupon the user can either select a time, change the search, or cancel. When a user completes the appointment scheduling process, the Web Server notifies 224 the Scheduling Ticket database that the appointment has been scheduled and the ticket for the current user is updated 226 accordingly. The Scheduling Ticket database will then track whether the appointment has been cancelled or completed, and will update the corresponding pre-qualified appointment record accordingly.

As previously mentioned, in addition to direct provider created tickets, patients may schedule an appointment through a user initiated scheduling process 112. An example of when this may be utilized is when a provider places a patient on a disease management protocol. These protocols might call for a patient to be seen with a certain frequency for specified types of visits. These protocols would automatically grant authority for the patients that conform to the limitations of the protocols. This process could be used independently or in combination with other insurance information available for the patient and represents the limitations that would be imposed on a patient self-scheduling through the web.

To provide additional control for healthcare providers, the system may be designed to apply a more restricted set of rules to patients scheduling appointments through the user initiated scheduling process. For example, a healthcare provider may reserve only a few time slots per week for patients to schedule appointments through this process. They may additionally limit those appointments to very short durations for limited purposes, such as consultations or the administration of simple tests. Another example is that the system could restrict a patient from selecting a provider or a department. Instead, the system would pick an appropriate provider or department from a pre-determined list that is driven by the patient as a parameter.

The patient would be provided access to a self scheduling application (e.g. a web site or a computer application for personal use, possibly running on a home computer, personal digital assistant (PDA) or cellular telephone) which would allow them to schedule the appointment.

This self-scheduling computer application would identify and authenticate the patient and read the database of electronic tickets to determine what self-scheduling limits exist for the patient. The self-scheduling application then allows the patient to select appointments that are within the limitation of the ticket.

Once an appointment is made, it is associated with the ticket. The ticket is then marked as "appointment made." When the appointment is kept, the ticket is marked as "appointment completed" and then subsequently destroyed or retained for historical analysis. If the patient or provider cancels the appointment, the ticket's status would revert to the "unused status."

The integration of the self-scheduling component into an overall healthcare management system is shown in FIG. 3. A completely integrated system provides patients with secure, real-time access to their Personal Health Record and an Enterprise Health Information System (PHR and EHIS, respectively). Access may be provided by way of the Internet 316 and via a Personal Health Portal (PHP) web page 318. From the secure PHP web page 318, patients can view information created and maintained by their health care providers and their affiliated staff. The patients can also request services and information from their health care providers and affiliated staff, directly access EHIS-related services, such as scheduling an appointment, paying a bill, enrolling in a class, completing insurance and other forms, and viewing information and Internet services that are relevant to their particular health status.

In a preferred embodiment of the invention a patient health record data server 302, including a machine readable media having a data structure containing patient-created data, is coupled by an electronic network with a patient interface. The electronic network may be the Internet 316 and the patient interface may be a suitable Internet access device including a browser for supporting a personalized web page 318. A secure interface securely couples, in real-time, the patient health record server 302 to an enterprise health record system 304 for providing access by the patient to patient-related data retained within the enterprise health record system 304. Thus, the patient, via the patient interface, may access the patient health record server 302 for manipulating the patient-created data and for accessing the patient-related data from the enterprise health record system 304.

Referring again to FIG. 3 of the drawings, the system includes a Patient Health Record (PHR) data server 302, an EHIS data server 306, and a self-scheduling server 308. The PHR data server 302 may be any suitable platform including processing, memory and data storage capability to perform the functions herein described. The PHR data server 302 stores data entered by the patient within a data structure configured within the storage portion of the PHR data server 302. A secure interface or EHIS queue securely couples the PHR server 302 and the EHIS data server 306 for communication of data and information from the PHR data server 302 to the EHIS data server 306. The EHIS queue provides a real-time secure communication link for information moving from the PHR data server 302 to the EHIS data server 306. This queue is used to transfer information for secure messaging and self-service options. In response to information received from the PHP web page 318, the PHR data server 302 forwards information to the EHIS queue. Information in the EHIS queue is then processed appropriately by the EHIS data server 306.

While the specific configuration of the EHIS data server 306 is not particular to the structure and function of the present invention, preferably, the EHIS data server 306 is a single data repository structured to support both the separation and the sharing of data. As such, the EHIS data server 306 may receive information from existing outpatient and inpatient data management systems via interfaces or from various integrated applications. The EHIS data server 306 may be configured to organize information into a consistent whole to provide a longitudinal patient record. For example, the EHIS data server 306 may be linked to manage all aspects of a patient's hospital health status and care and to support effective management of patient lists, results inquiry management, complete clinical documentation, physician order entry with decision support, nursing workflow and documentation, and discharge planning.

The EHIS data server 306 may further be configured to support the inclusion of problem lists, order communications, results reporting, pharmacy management, quick documentation, clinical messaging and communication. Additionally, the EHIS data server 306 may be configured to manage referral information, up-to-date progress notes, lab results, discharge instructions, portions of a patient's record, and emergency summary cards. A suitable data management product that may be adapted as the EHIS data server 306 is the Epicenter® Enterprise Data Repository and related suite of products available from Epic Systems Corporation of Madison, Wis.

The specific configuration of the scheduling server 308 is also not particular to the structure and function of the present invention. However, the scheduling server may be any suitable platform that includes a processor, memory and data storage capability to perform the functions herein described. These functions may alternatively be performed by the EHIS server 306. Thus, the scheduling server 308 may be a separate component from the EHIS server 306, or it may be one in the same.

An electronic network couples the PHR data server 302, the EHIS server 306, and the scheduling server 308 to a patient interface. While FIG. 3 depicts the scheduling server 308 as a separate component, as mentioned above, an alternative embodiment may include the scheduling server as part of the EHIS server 306, as represented by the phantom line 304 in FIG. 3. The electronic network may include the Internet 316 or another suitable data network. The system servers are electronically linked to the Internet by a web server 312 in a highly secure dual firewall configuration. In this arrangement, a primary fire wall 314 protects the web server 312 and a secondary fire wall 310 protects the PHR data server 302, EHIS server 306, and scheduling server 308. Additionally, the PHR data server 302, EHIS server 306, and scheduling server 308 are also electrically interconnected.

Patients access the system by logging into the web server 312 via the patient interface. The patient interface is preferably configured as a web page displayed within a web browser running on a suitable platform, and is further preferably configured as a personalized Personal Health Portal (PHP) web page 318 providing the patient with patient-specific information and links to the features and services offered by the invention. The web server 312 may be any suitable web server platform containing routines for displaying the PHP web page 318 and for managing online communication between a user logged in via an associated PHP web page 318, the PHR data server 302, and the EHIS data server 306.

Rules-based scheduling tickets solve the many problems that the healthcare industry has encountered. First, the scheduling ticket could be sent to the facility via a secure web-access application ensuring that the request will remain confidential. Furthermore, the self-scheduling functionality is equipped with a dynamic feedback system, which prevents patients from abusing their self-scheduling capabilities. For instance, if a patient schedules multiple appointments and does not show up for the appointments, the patient could be banned from scheduling any more appointments over the Internet. Finally, because of the hierarchical rules that a facility could enact, the facilities, departments, and providers are able to determine which patients can use scheduling tickets and which time slots they can schedule in at different levels, so that they do not lose control of their daily schedules.

The invention has been described in terms of several preferred embodiments. It will be appreciated that the invention may otherwise be embodied without departing from the fair scope of the invention defined by the following claims.

We claim:

1. A method of allowing patients to schedule their own medical appointments on a computerized scheduling system, the method comprising the steps of operating the computerized scheduling system to:

communicate directly with the patient over the Internet to accept a patient request to schedule a medical appointment of a requested type;

automatically review a record of the patient's completion of previous appointments;

automatically compare a measure of the patient's completion of previous appointments to a predetermined threshold;

automatically determine whether the measure of the patient's completion of previous appointments exceeds the predetermined threshold;

when the measure of the patient's completion of previous appointments exceeds the predetermined threshold, automatically accept the patient's request for the medical appointment on behalf of the patient;

when the measure of the patient's completion of previous appointments does not exceed the predetermined threshold, deny the patient's Internet request to schedule the medical appointment and require the patient to schedule the medical appointment through a human intermediary.

2. The method of claim 1 wherein the method further includes operating the computerized scheduling system to:

create at least one electronic ticket identifying a given patient and allowing the patient to schedule at least one medical appointment of a predetermined type as determined by the physician; the ticket having a status of unused or appointment completed; and automatically schedule the medical appointment on behalf of the patient only if the status is unused and the requested type is the predetermined type of the electronic ticket.

3. The method of claim 2 further including the step of:

when the appointment is scheduled, changing the ticket status to appointment completed when the patient completes the appointment.

4. The method of claim 3 further including the step of:

after enrollment, accepting instructions from the patient to cancel an enrolled appointment and changing the status of the ticket to unused.

5. The method of claim 1 wherein the method further includes operating the computerized scheduling system to:

automatically schedule the medical appointment on behalf of the patient only if appointment times are available in a first set of appointment times; and when appointment times are not available in the first set of appointment times, refer the patient to a human intemiediary to schedule the medical appointment in second times other than the first set of appointment times.

6. The method of claim 1 wherein the medical appointment is scheduled in a database providing an integrated patient medical record.

7. A computerized scheduling system allowing patients to schedule their own medical appointments comprising a stored program executing on an electronic computer, the stored program executing the program to:

communicate directly with the patient over the Internet to accept a patient request to schedule a medical appointment of a requested type;

automatically review a record of the patient's completion of previous appointments;

automatically compare a measure of the patient's completion of previous appointments to a predetermined threshold;

automatically determine whether the measure of the patient's completion of previous appointments exceeds the predetermined threshold;

when the measure of the patient's completion of previous appointments exceeds the predetermined threshold, automatically accept the patient's request for the medical appointment on behalf of the patient;

when the measure of the patient's completion of previous appointments does not exceed the predetermined threshold, deny the patient's Internet request to schedule the medical appointment and require the patient to schedule the medical appointment through a human intermediary.

8. The computerized scheduling system of claim 7 wherein the stored program further executes to:

create at least one electronic ticket identifying a given patient and allowing the patient to schedule at least one medical appointment of a predetermined type as determined by the physician; the ticket having a status of unused or appointment completed; and automatically schedule the medical appointment on behalf of the patient only if the status is unused and the requested type is the predetermined type of the electronic ticket.

9. The computerized scheduling system of claim 8 wherein the stored program further executes to:

when the appointment is scheduled, change the ticket status to appointment completed when the patient completes the appointment.

10. The computerized scheduling system of claim 9 wherein the stored program further executes to:

after enrollment, accept instructions from the patient to cancel an enrolled appointment and changing the status of the ticket to unused.

11. The computerized scheduling system of claim 7 wherein the stored program further executes to:

automatically schedule the medical appointment on behalf of the patient only if appointment times are available in a first set of appointment times; and when appointment times are not available in the first set of appointment times, refer the patient to a human intermediary to schedule the medical appointment in second times other than the first set of appointment times.

12. The computerized scheduling system of claim 7 wherein the medical appointment is scheduled in a database providing an integrated patient medical record.

* * * * *